United States Patent
Garino

(10) Patent No.: US 9,968,389 B2
(45) Date of Patent: May 15, 2018

(54) FRACTURE PLATING

(71) Applicant: Jonathan P. Garino, Villanova, PA (US)

(72) Inventor: Jonathan P. Garino, Villanova, PA (US)

(*) Notice: Subject to any disclaimer, the term of this patent is extended or adjusted under 35 U.S.C. 154(b) by 0 days. days.

(21) Appl. No.: 15/258,066

(22) Filed: Sep. 7, 2016

(65) Prior Publication Data
US 2016/0374739 A1 Dec. 29, 2016

Related U.S. Application Data
(63) Continuation of application No. 14/562,940, filed on Dec. 8, 2014, now Pat. No. 9,463,053.

(51) Int. Cl.
*A61B 17/70* (2006.01)
*A61B 17/80* (2006.01)
*A61B 17/72* (2006.01)
*A61B 17/84* (2006.01)
*A61B 17/68* (2006.01)

(52) U.S. Cl.
CPC .............. *A61B 17/80* (2013.01); *A61B 17/72* (2013.01); *A61B 17/7241* (2013.01); *A61B 17/8004* (2013.01); *A61B 17/809* (2013.01); *A61B 17/84* (2013.01); *A61B 2017/681* (2013.01)

(58) Field of Classification Search
CPC . A61B 17/8061; A61B 17/80; A61B 17/8057; A61B 17/7059; A61B 17/1728
USPC .................... 606/280–299, 70, 71
See application file for complete search history.

(56) References Cited

U.S. PATENT DOCUMENTS

| | | | |
|---|---|---|---|
| 5,522,902 A | 6/1996 | Yuan | |
| 6,007,536 A | 12/1999 | Yue | |
| 8,147,493 B2 * | 4/2012 | Dutoit | A61B 17/746 606/284 |
| 8,709,092 B2 | 4/2014 | Segina | |
| 8,808,333 B2 | 8/2014 | Kuster | |

(Continued)

FOREIGN PATENT DOCUMENTS

| | | |
|---|---|---|
| DE | 202 014 00093 | 5/2014 |
| GB | 1 274 470 | 5/1972 |

OTHER PUBLICATIONS

Ha et al., "Minimally Invasive Plate Osteosynthesis for Periprosthetic Distal Femoral Fractures after Total Knee Anthroplasty," Knee Surg Relat Mar. 2014, vol. 26, No. 1, pp. 27-32.

Hou et al., "Locked plating of Periprosthetic femur fractures above total knee arthyoplasty," J Orthop Trauma, Jul. 2012, vol. 26, No. 7, pp. 427-432 (Abstract only).

(Continued)

*Primary Examiner* — Eduardo C Robert
*Assistant Examiner* — Tara R Carter
(74) *Attorney, Agent, or Firm* — RatnerPrestia

(57) ABSTRACT

A plating system for mending a periprosthetic fracture is provided. The system includes an intramedullary rod, a first and second plate, and a plurality of fasteners. The intramedullary rod has a plurality of transverse holes. The first and second locking plates each have a plurality of openings and is configured to have a contour similar to a surface of a bone to which the plate is applied. Also provided is method of mending fractures by using the disclosed system. In the implanted condition, the first and second locking plates are placed across the periprosthetic fracture and each of the plurality of fasteners is inserted through one opening of the first and second plurality of openings and one transverse hole.

7 Claims, 1 Drawing Sheet

(56) References Cited

U.S. PATENT DOCUMENTS

| | | | |
|---|---|---|---|
| 2003/0135212 A1* | 7/2003 | Chow | A61B 17/72 606/64 |
| 2006/0100623 A1 | 5/2006 | Pennig | |
| 2007/0225819 A1 | 9/2007 | Eva | |
| 2009/0177240 A1* | 7/2009 | Perez | A61B 17/7233 606/86 R |
| 2009/0275991 A1* | 11/2009 | Medoff | A61B 17/1775 606/297 |
| 2010/0262194 A1 | 10/2010 | Wagner | |
| 2010/0318086 A1* | 12/2010 | Winemaker | A61B 17/683 606/70 |
| 2011/0137314 A1 | 6/2011 | Kuster et al. | |
| 2014/0243829 A1 | 8/2014 | Cavallazzi | |

OTHER PUBLICATIONS

International Search Report for PCT Application No. PCT/US2015/064387 dated Feb. 10, 2016.

McGraw et al., "Periprosthetic fractures of the femur after total knee arthroplasty," J Orthop Traumatol, Sep. 2010, vol. 11, No. 3, pp. 135-141.

Noorda et al., "Mennen Plate Fixation for the Treatment of Periprosthetic Femoral Fractures," J Bone Joint Aug Am, Dec. 2002, vol. 84, No. 12, pp. 2211-2215.

Ruchholtz et al., "Periprosthetic fractures around the knee—the best way of treatment," European Orthopaedics and Traumatology, Jun. 2013, vol. 4, Issue 2, pp. 93-102 (Abstract only).

International Preliminary Report on Patentability for International Application No. PCT/US2015/064387, dated Jun. 13, 2017, 8 pages.

* cited by examiner

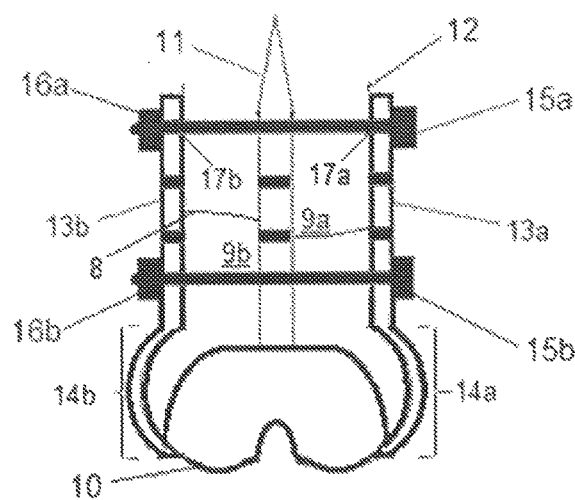
Figure 1
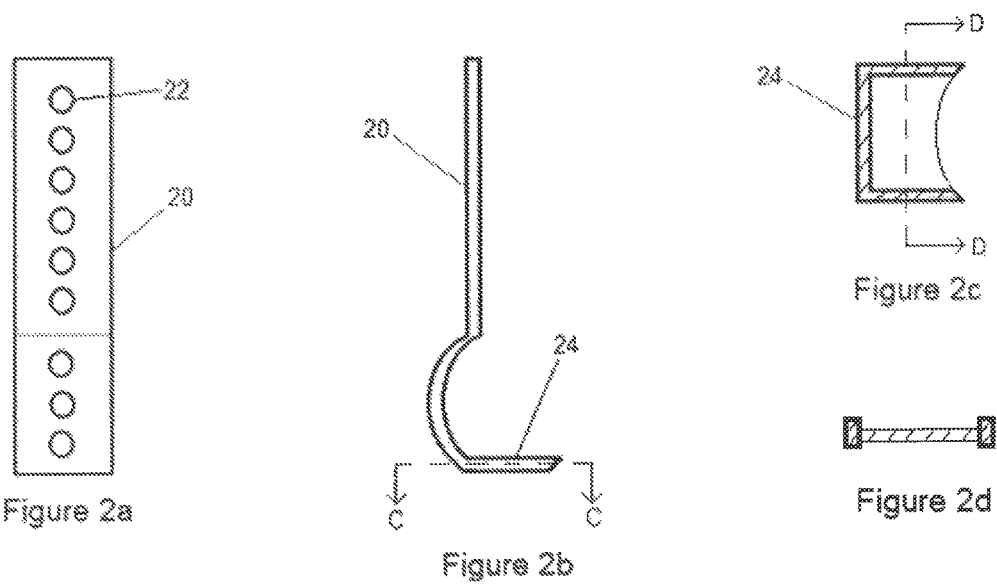
Figure 2a
Figure 2b
Figure 2c
Figure 2d

FRACTURE PLATING

CROSS-REFERENCE TO RELATED APPLICATIONS

This application is a continuation of U.S. application Ser. No. 14/562,940, filed Dec. 8, 2014, the disclosure of which is incorporated herein by reference in its entirety for all purposes.

FIELD OF THE INVENTION

The invention relates to plates that are surgically implanted, in particular, plates that are implanted to mend periprosthetic fractures.

BACKGROUND

A common problem associated with joint replacement surgery is the development of fractures around the prosthetic, known as periprosthetic fractures. For example in a Total Knee Replacement (TKR) procedure, fractures may occur in the femur around the prosthetic joint implanted at the distal portion of the femur. Various treatments are employed depending on the severity of the fractures and whether the prosthetic becomes loose. The fractures generally occur as a result of trauma or infection and in extreme cases may require additional surgical procedures in order to re-align the prosthetic knee and/or apply additional plates or rods, so that the fractures will heal properly. In most cases when a periprosthetic knee fracture occurs, the prosthesis remains well fixed to the bone beneath it and securing the bone to the part of the femur which has broken away is a challenge.

Mending such fractures is a challenge due to the lack of available healthy bone remaining around the location of the fractures. As a result, fracture fixation may be inadequate and the fracture may heal incorrectly causing abnormal stresses on the prosthetic joint, which in turn may cause pain, stiffness, and potential TKR failure. Therefore, there is a need for improved surgical implants to mend periprosthetic fractures.

SUMMARY OF THE INVENTION

According to an embodiment of the present invention, a plating system for mending a periprosthetic fracture is provided. The system comprises an intramedullary rod including a plurality of transverse holes, a first locking plate having a first plurality of openings and configured to have a contour similar to a first surface of a bone, and a second plate having a second plurality of openings and configured to have a contour similar to a second surface of the bone. The system further includes a plurality of fasteners, wherein in the implanted condition, the first and second locking plates are placed across the periprosthetic fracture and each of the plurality of fasteners is inserted through one opening of the first and second plurality of openings and one transverse hole.

According to another embodiment of the present invention, a method of mending a periprosthetic fracture is provided. The method comprises applying a first locking plate to a first surface of the bone across the periprosthetic fracture, the first locking plate having a first plurality of openings and configured to have a contour similar to the first surface of a bone, applying a second plate to a second surface of the bone across the periprosthetic fracture, the second locking plate having a second plurality of openings and configured to have a contour similar to the second surface of the bone, inserting an intramedullary rod having a plurality of transverse holes into the medullary cavity of the bone, and attaching the first locking plate to the second locking plate via plurality of fasteners. Each of the each of the plurality of fasteners is inserted through one opening of the first and second plurality of openings and one transverse hole.

BRIEF DESCRIPTION OF THE FIGURES

FIG. 1 is a front cross-sectional view of a first embodiment of the invention in the installed condition;

FIG. 2a is a side plan view of fracture plate included in a system according to another embodiment of the present invention;

FIG. 2b is a front view of the fracture plate of FIG. 2a; and

FIG. 2c is a cross-sectional view of the fracture plate along axis c-c in FIG. 2b.

FIG. 2d is a cross-sectional view of the fracture plate along axis d-d in FIG. 2c.

DETAILED DESCRIPTION

The invention will now be described by reference to exemplary embodiments and variations of those embodiments. Although the invention is illustrated and described herein with reference to specific embodiments, the invention is not intended to be limited to the details shown and described. Rather, various modifications may be made in the details within the scope and range of equivalents of the claims and without departing from the invention.

Generally, various embodiments of the present invention provide a means for mending periprosthetic fractures. The means for mending the periprosthetic fractures may comprise locking plates that may be configured for attachment to a plurality of bone fragments separated by a fracture. The locking plates assist in fixing the bone fragments in their relative position by preventing movement of the fragments relative to one another within the six degrees of freedom. The locking plates may be implanted by attaching at least two plates to the bone fragments across a periprosthetic fracture, preferably on opposing sides of the bone. The locking plates may be contoured, so that the locking plates will follow the contour of the bone to which the locking plates are applied. The locking plates may also be configured to be implanted in close proximity to a prosthetic joint without touching the prosthesis, such that the locking plates do not interfere with the operation of the artificial joint.

Referring now to FIG. 1, an exemplary embodiment of a plating system according to the present invention is illustrated comprising a medical device that is surgically implanted onto the bone 12 and spans a fracture 8 in order to treat, for example, a distal femoral fracture.

The plating system of the embodiment of FIG. 1 comprises two locking plates 13a, 13b, applied to opposing sides of the distal end of a femur 12 near the femoral component 10 of a prosthetic knee. In FIG. 1, one of the locking plates 13a may be applied to the medial side of the femur on the bone fragments 9a, 9b of the bone 12, while the other locking plate 13b may be also be applied to bone fragments 9a, 9b, but on the lateral side of bone 12. Locking plates used in systems according to the present invention are not limited to attachment to the material and medial sides of the bone. The plates may be configured for attachment to any side or section of a bone, as long as the locking plates are installed across a fracture with one end section attached to a first bone fragment and a second end section of the locking plate attached to the second adjacent bone fragment.

The system may further comprise an intramedullary (IM) nail or rod 11. An IM rod, as known by those of skill in the art, is a metal rod forced into the medullary cavity of a bone. IM rods assist in fixing the fragments of a bone separated by a fracture. The IM rod 11 may have a plurality of transverse holes extending through the rod to accommodate one or more fasteners 15a, 15b. The fasteners are preferably provided in the form of transfixing bolts. Inserting one of the fasteners 15a through the first bone fragment 9a on one side of the fracture 8 and the second fastener 15b through the adjacent bone fragment 9b on the other side of the fracture 8 may prevent rotation of the bone fragments relative to one another about the longitudinal axis of the IM rod 11. This rotation may be referred to as yaw, one of the six degrees of freedom. The fasteners 15a, 15b may also assist the IM rod 11 in preventing the fragments from separating from each other along the longitudinal direction of the IM rod 11.

Referring to the cross-sectional view illustrated in FIG. 1, the combination of the fasteners 15a, 15b and the IM rod 11 may prevent movement in two of the six degrees of freedom. However, the combination of the fasteners 15a, 15b and the IM rod 11 may not sufficiently minimize or eliminate relative movement between the two bone fragments 9a, 9b in the X-direction (left to right) or the Z-direction (forward and back). Rotation about the X-axis and the Z-axis (pitch and roll) may also not be sufficiently prevented by the combination of the IM rod 11 and fasteners 15a, 15b. In order to minimize or eliminate the potential relative movement for all six degrees of freedom between the bone fragments 9a, 9b, it is preferable that the transfixing bolts 15a, 15b are also inserted through openings 17a, 17b in the locking plates 13a, 13b.

The locking plates 13a, 13b may be compressed against the bone 12. In one embodiment of the present invention, the compression may be achieved by inserting each fastener 15a, 15b through a corresponding opening 17a, 17b in each locking plate 13a, 13b and through a hole in the IM rod 11. It is preferred that the spacing between the holes in the IM rod 11 is about the same as the spacing between the openings in each of the locking plates 13a, 13b. This ensures that the transfixing bolts 15a, 15b are relatively perpendicular to the longitudinal axis of the IM rod 11 when installed. The diameter of the head of the fasteners 15a, 15b may be larger than the diameter of the openings in each locking plate 15a, 15b. This will allow the transfixing bolts 15a, 15b to be inserted in either direction. A nut 16a, 16b may then be screwed on the opposing end of each fastener 15a, 15b. The nut, like the head of the fasteners 15a, 15b, may have a diameter larger than the opening of the locking plates 13a, 13b, so that a compressive force on either side of the locking plates 13a, 13b is generated when the nuts 16a, 16b are tightened. The fasteners 15a, 15b preferably include some feature that will prevent the nuts 16a, 16b from slipping to maintain the compressive force generated once set by a user. The feature should prevent the loss of compressive force for at least as long as necessary for the fracture to heal. Such features may include the standard features associated with a locknut or lock washer as are known in the art, a set screw inserted through a tapped hole in the nut perpendicular to and in contact with the shaft of the fastener, or any feature capable of providing the desired functionality.

As mentioned above, it is preferred that the locking plates 13a, 13b are manufactured to be attached as close to the prosthetic joint 10 as possible, so that extreme distal and proximal fractures in the bones may be repaired. To enable attachment close to the prosthetic joint, the locking plates 13a, 13b may be contoured to match the contour of the bone to which it is attached. For example, in the embodiment illustrated in FIG. 1, the locking plates 13a, 13b each include a bent section 14a, 14b that may be applied around and over at least a portion of either the medial or lateral condyle of the femur 12.

Referring now to FIGS. 2a to 2c, a locking plate 20 according to another embodiment of the present invention may include a plurality of openings 22 for receiving a fastener and a blade 24 to enhance the grip of the device on the fractured bone. The blade 24 may be located on at least one end portion of the locking plate 20. A cross-sectional view of an exemplary blade 24 along axis c-c in FIG. 2b is illustrated in FIG. 2c. A cross-sectional view of an exemplary blade 24 along axis d-d in FIG. 2c is illustrated in FIG. 2d. The blade 24 may include two ¼ inch end projections roughly 8 mm apart resulting in a cross-section that is 'C-shaped' when viewed in the cross section of FIG. 2c. The length of the blade is preferably about 1" to 2" long. The C-shaped structure of the blade 24 is preferred as it minimally disrupts existing bone while maximizing the area-moment of inertia because the C-shaped blade 24 will more closely resemble the outside curvature of the bone at the location in which the blade is to be inserted. The blade 24 once inserted into the bone and following insertion of a fastener, such as a transfixing bolt, through one of the plurality of openings 22 will prevent the locking plate 20 from rotating or pivoting on the surface of the bone.

The transfixing bolts may provide a dual fixation aspect whereby the bolts compress the locking plates pushing the blade into the bone, so that the end of the locking plates grip the distal end of the bone and simultaneously, the bolts exert additional stability through compression as described above. Finally, the blade may be a separate piece attached to the plate with an additional fastener inserted, for example, through any of the holes in the locking plate. A separate blade allows the surgeon performing the periprosthetic fracture repair procedure to select the position of the blade and customize the location at which the blade may grip the bone.

In yet another exemplary embodiment of the present invention, a method of mending a perisprothetic fracture is provided. The method may comprise first inserting an IM rod into the medullary cavity of the bone having the fracture, followed by placing locking plates across the fracture on either side of the bone. The locking plates may then be fastened together by using one or more fasteners, such as transfixing bolts. Therefore, a user may select one or more from a plurality of openings in each locking plate through which a fastener may be inserted, ensuring that the fastener is also inserted through a transverse hole in the IM rod. After the one or more fasteners are inserted through the locking plates and the IM rod, a compressive force is applied to the locking plates in order to hold the plates in position on the surface of the bone. Preferably, the fasteners holding the locking plates in position are oriented perpendicular or approximately perpendicular to the longitudinal axis of the IM rod.

It is preferred that the locking plates and the IM rod include a plurality of openings to receive the fasteners to allow the surgeon to customize the location of the plates along the bone. In FIG. 1, for example, the locking plates 13a and 13b have been placed at the same height on the bone 12. However, embodiments of the present invention may include locking plates that a configured to be moved independently of one another either distally or proximally along the bone according to the needs of the patient and the location and severity of the fracture. In general, when mending a periprosthetic fracture, the medial locking plate will be slightly further distal than the lateral locking plate. An aspect of a fracture plating system according to the present invention is that the femoral component may be restored to its correct position and rigidly fixed in place to allow the fracture to heal by providing improved and reliable alignment of the bone, such as a femur in the coronal and sagittal planes.

While preferred embodiments of the invention have been shown and described herein, it will be understood that such embodiments are provided by way of example only. Numerous variations, changes, and substitutions may occur to those skilled in the art without departing from the spirit of the invention. Accordingly, it is intended that the appended claims cover all such variations that fall within the spirit and scope of the invention.

I claim:

1. A plating system for mending a periprosthetic fracture comprising:
    an intramedullary rod including a plurality of transverse holes;
    a first locking plate having a first plurality of openings and configured to have a contour similar to a first surface of a bone; and
    a second plate having a second plurality of openings and configured to have a contour similar to a second surface of the bone;
    a plurality of fasteners; and
    a plurality of nuts, each nut being configured to be attached to an end of a respective fastener of the plurality of fasteners,
    wherein in an implanted condition, the first and second locking plates are disposed across the periprosthetic fracture and each of the plurality of fasteners extends through one opening of the first plurality of openings, another opening of the second plurality of openings, and one transverse hole, and is attached to one of the plurality of nuts,
    wherein at least one of the first and second locking plates include a bone gripping mechanism, the bone gripping mechanism comprising a blade having a free end configured for insertion into the bone,
    wherein the blade comprises two projections and a C-shaped web of material extending in a width direction between the two projections and extending in a length direction along said two projections to the free end of the blade, each projection having a greater thickness than the C-shaped web of material.

2. The plating system of claim 1, wherein the bone gripping mechanism is configured to be set at a user-selected location on one of the first and second locking plates.

3. The plating system of claim 1, wherein the plurality of fasteners are configured to compress the first and second locking plates toward one another when in a tightened configuration.

4. The plating system of claim 3, wherein the plurality of fasteners are configured to maintain a force of compression until at least the fracture is healed.

5. The plating system of claim 1, wherein the plating system is configured to prevent relative movement of bone fragments within six degrees of freedom.

6. The plating system of claim 1, wherein the intramedullary rod has a longitudinal axis and in the implanted condition the plurality of fasteners are perpendicular to the longitudinal axis.

7. The plating system of claim 1, wherein the plating system is configured to be implanted in proximity to a prosthesis such that in the implanted condition the first locking plate and second locking plate do not touch the prosthesis.

* * * * *